United States Patent
Knodel et al.

[11] Patent Number: 5,814,055
[45] Date of Patent: Sep. 29, 1998

[54] SURGICAL CLAMPING MECHANISM

[75] Inventors: Bryan D. Knodel, Cincinnati; J. David Hughett, Hamilton; Anil K. Nalagatla, West Carrollton, all of Ohio

[73] Assignee: Ethicon Endo-Surgery, Inc., Cincinnati, Ohio

[21] Appl. No.: 713,055

[22] Filed: Sep. 12, 1996

Related U.S. Application Data

[63] Continuation-in-part of Ser. No. 530,931, Sep. 19, 1995.

[51] Int. Cl.⁶ .................................................. A61B 17/08
[52] U.S. Cl. ........................ 606/151; 606/142; 606/139; 227/901
[58] Field of Search ..................................... 606/151, 142, 606/143, 139, 158, 157; 227/901, 902, 175.1, 175.3, 176.1, 175.2, 177.1, 180.1, 181.1, 182.1

[56] References Cited

U.S. PATENT DOCUMENTS

| | | | |
|---|---|---|---|
| 352,245 | 11/1886 | Hullhorst | 606/142 |
| 4,169,476 | 10/1979 | Hiltebrandt | 128/325 |
| 4,784,137 | 11/1988 | Kulik et al. | 128/334 |
| 5,040,715 | 8/1991 | Green et al. | 227/176 |
| 5,071,430 | 12/1991 | de Salis et al. | 606/219 |
| 5,307,976 | 5/1994 | Olson et al. | 227/178 |
| 5,308,576 | 5/1994 | Green et al. | 419/38 |
| 5,425,745 | 6/1995 | Green et al. | 606/219 |
| 5,449,365 | 9/1995 | Green et al. | 606/142 |
| 5,465,895 | 11/1995 | Knodel et al. | 227/176 |
| 5,485,952 | 1/1996 | Fontayne | 227/178.1 |

*Primary Examiner*—Michael Powell Buiz
*Assistant Examiner*—Tina T. D. Pham
*Attorney, Agent, or Firm*—Matthew S. Goodwin

[57] ABSTRACT

A surgical stapling instrument which has an elongated staple cartridge and anvil is disclosed. The anvil is movable relative to the cartridge from rearward to forward positions for insertion of tissue between these two components and clamping the tissue, respectively. A pair of spaced-apart ribs protrude from the anvil, and when the anvil is moved from its rearward to forward positions, these ribs are received into and slide within a groove embedded on the surface of the cartridge. In this manner, misalignment of the anvil and cartridge when tissue is being clamped is prevented or appreciably reduced, therefore reducing the chances of misforming the staples when the instrument is fired. The alignment features also act as tissue abutment surfaces to prevent the migration of tissue into a region where tissue is transected but not stapled.

3 Claims, 10 Drawing Sheets

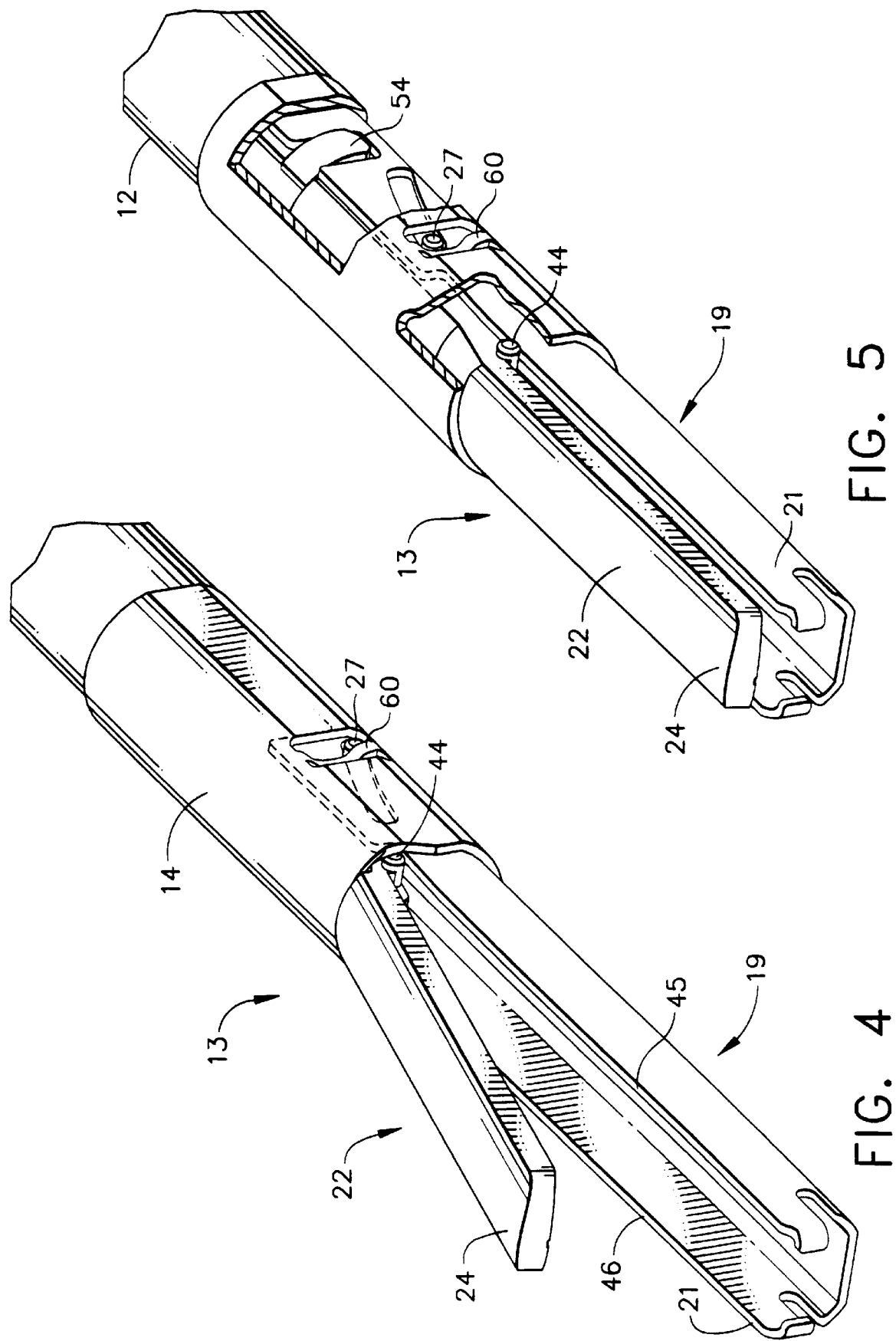

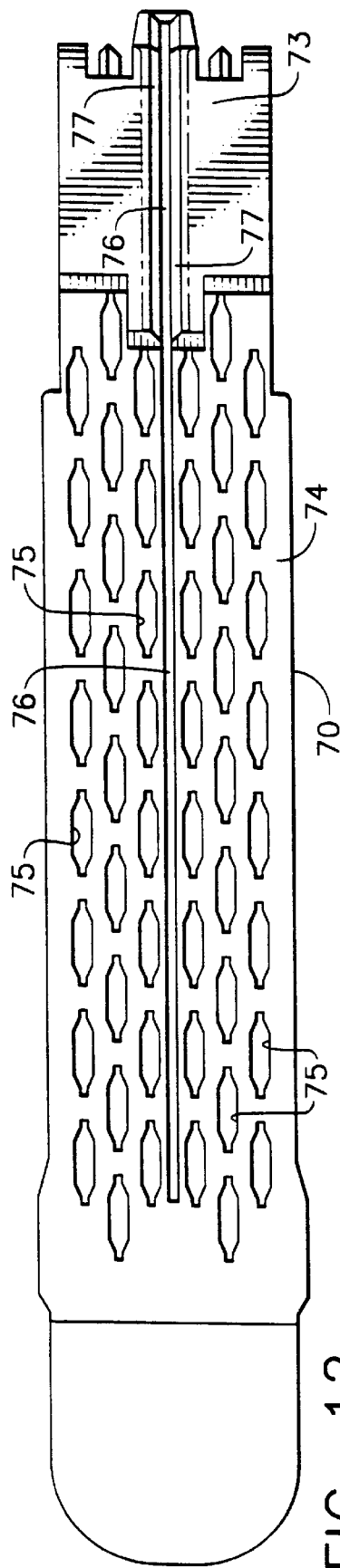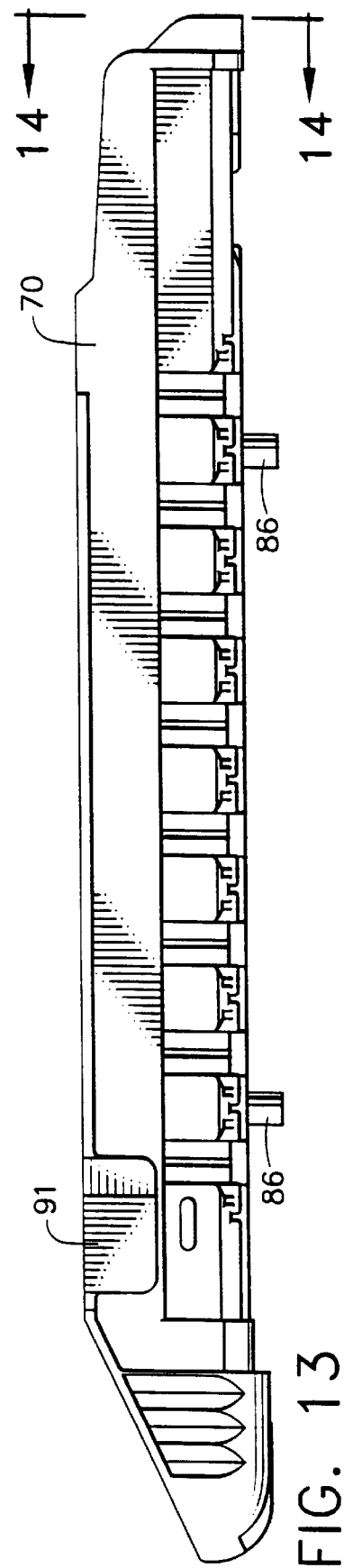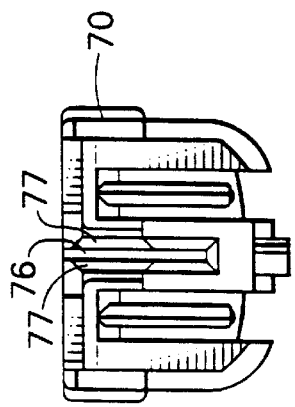
FIG. 12
FIG. 13
FIG. 14

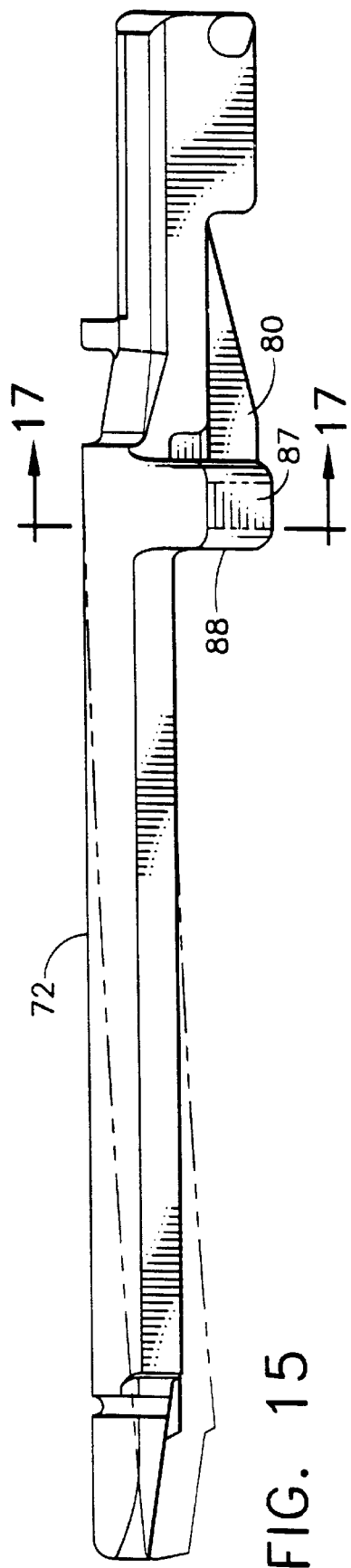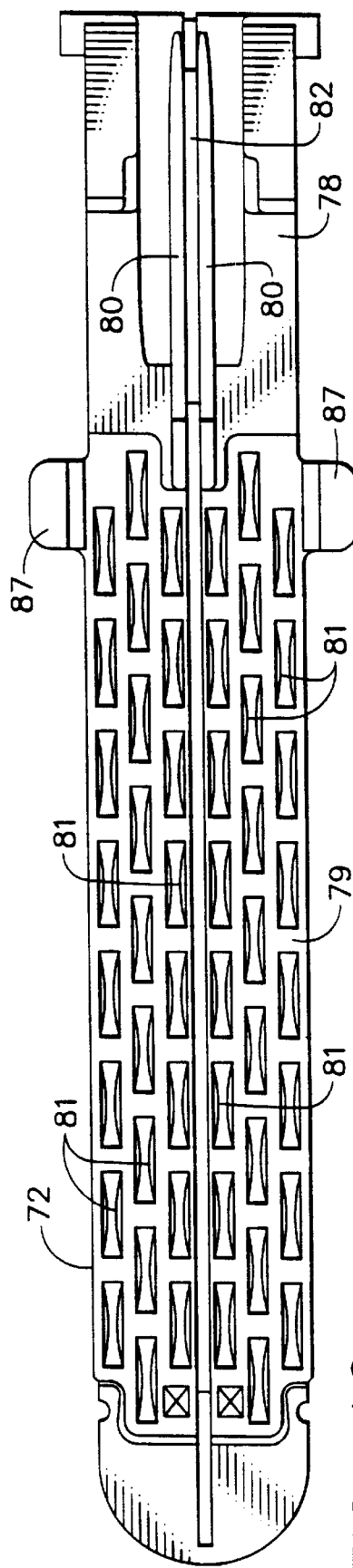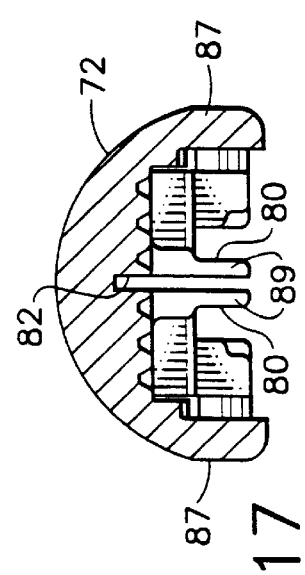

SURGICAL CLAMPING MECHANISM

CROSS REFERENCE TO RELATED APPLICATION

This is a continuation-in-part of application Ser. No. 08/530,931, filed Sep. 19, 1995.

BACKGROUND OF THE INVENTION

This invention relates to instruments for performing surgical procedures. More particularly, it relates to the clamping mechanism of these instruments which enables the surgeon to clamp or grasp bodily tissue especially during endoscopic surgical procedures.

During an endoscopic surgical procedure, access to the surgical site within the body cavity is provided through openings of a small diameter made in the body wall. An instrument frequently used to provide this access is the trocar. The trocar is an assembly which includes an obturator and a cannula. The obturator has a sharp tip which is used to puncture the body wall to provide the access opening. The obturator slides within the cannula, which is a hollow, cylindrical sleeve. When the obturator has punctured the body wall, the obturator is removed from the cannula. The cannula, however, remains in place within the opening made in the body wall by the obturator. Consequently, the cannula provides a cylindrical passageway to gain access to the surgical site within the body cavity.

Accordingly, a characteristic feature of many endoscopic surgical instruments is a long cylindrical shaft which can slide through the trocar cannula. At the business end of the shaft, which is the end of the instrument coming into contact with tissue at the surgical site within the body cavity, an "end effector" is provided to manipulate the tissue in some way to carry out a desired surgical procedure. The business end including the end effector, must likewise be capable of sliding through the trocar cannula. At the opposite end of the shaft, there is an actuator operatively connected to the business end to remotely control the performance of the end effector. The actuator is conveniently housed in a frame which may include a pistol grip handle with one or more pivoting triggers. Alternatively, the actuator may include a lever, or the combination of a pivoting trigger and a lever. The actuator is activated when the surgeon pivots the trigger or depresses the lever. These actions in turn cause the end effector to perform its desired function.

One particularly desired function of an end effector of an endoscopic surgical instrument is the ability of the end effector to clamp or grasp tissue. It may be necessary to grasp tissue so that it may be retracted or otherwise precisely positioned to carry out a particular procedure. Instruments which carry out these functions are conveniently referred to as graspers and retractors. In some procedures, it is desirable to clamp tissue so that the clamped tissue may be fastened when staples are fired into and through the tissue. Instruments with end effectors which fire staples into clamped tissue are referred to as linear staplers and cutters (cutters are so named because they simultaneously cut the tissue with a knife between rows of fired staples).

The end effector of an endoscopic surgical instrument which can clamp or grasp tissue typically has two opposed, elongated jaws. The jaws have internal tissue-contacting surfaces between which the tissue is clamped or grasped. The jaws are often described as a lower jaw and an upper jaw. The lower and upper jaws move relative to each other. When the jaws are moved to an open position, the tissue clamping surfaces of the jaws are spaced from each other so that tissue can be placed between the two surfaces. When the jaws are moved to their closed position, the tissue-contacting surfaces of the jaws are positioned adjacent each other so that tissue placed between the jaws is clamped or grasped. Often, the tissue-contacting surfaces of graspers may be serrated to provide an enhanced surface for grasping tissue, and both jaws pivot between their opened and closed positions. Linear cutters and staplers have conventionally had a fixed lower jaw and a pivoting upper jaw which pivots from open to closed positions relative to the lower jaw. The fixed lower jaw may include a channel for receiving a staple cartridge. The upper jaw typically includes an anvil. Accordingly, when a linear stapler or cutter is used, tissue is placed between the cartridge and anvil when the upper jaw is in the open position, the upper jaw is pivoted to its closed position to clamp tissue between the cartridge and anvil, and staples are subsequently fired from the cartridge into the clamped tissue for formation against the anvil.

A key feature of the clamping and grasping mechanisms of endoscopic surgical instruments is the mechanism which causes the upper or lower jaw to move from an open position for placing tissue between the jaws to a closed position for clamping that tissue. A common mechanism, particularly for endoscopic linear cutters, involves the use of a "camming" closure tube. This tube reciprocates back and forth. In its rearward position, the jaws are in the open position. In its forward most position, the upper jaw has pivoted to its closed position so that the anvil and cartridge are adjacent each other. In its rearward position, the distal end of the tube is positioned proximally of the upper jaw (in other words, the tube sits behind the jaw). The upper jaw, which is more frequently referred to simply as the anvil, has what is referred to as an outer, ramped camming surface at its proximal end. When the tube reciprocates from its rearward to forward position, the distal end of the tube slides along, or "cams" against the outer camming surface of the anvil. This camming action causes the anvil to pivot from its open to closed position.

Unfortunately, the camming mechanism for causing opposed jaws to clamp or grasp tissue placed between them is undesirably inefficient. There are high frictional losses associated with the camming action as the distal end of the tube slides against the ramped camming surface of the anvil. These high frictional losses create poor efficiency for the mechanism. When the mechanism is inefficient, higher forces are necessary to actuate the clamping mechanism. In other words, the surgeon using the instrument will need to exert more pressure when he squeezes the trigger or depresses the lever to actuate the clamping mechanism so that the jaws close. Obviously, precise positioning of the end effector is hampered and frustration mounts as the amount of pressure which the surgeon must apply to clamp increases.

Another difficulty with the use of the closure tube for camming is the requirement for the ramped camming surface on the anvil. This surface is really "wasted" surface area on the anvil because that portion of the anvil where this surface is positioned may not be used to form staples. The staple-forming surface of the anvil, which is the internal tissue-contacting surface, has pockets or depressions embedded in it where staples fired from the cartridge are formed. The inner surface of the portion of the anvil which is opposite the outer, ramped camming surface cannot, by its nature contain the pockets or depressions for staple formation. Therefore, staples are not formed along the entire length of the inner surface of the anvil. This means that the anvil is longer than it needs to be. Consequently, when tissue is clamped between the jaws, the jaws may undesirably "flex" or twist. This can frequently be a problem when thick tissue is clamped between the jaws, because the force necessary to clamp thick tissue is greater than the force necessary to clamp thin tissue. When flexing or twisting of the jaws occurs, it may cause the staples to malform when they are fired, resulting in improperly fastened tissue.

Another problem with the ramped camming surface is that because it necessitates the use of an anvil which is longer than the tissue-contacting surface of the cartridge, it becomes necessary to incorporate a "tissue stop" onto the anvil. The tissue stop retards the passage of the tissue placed between the jaws into that portion of the anvil opposite the ramped camming surface where staples cannot be fired. The tissue stop is typically a pair of lateral surfaces descending from the elongated anvil body. These lateral surfaces come into contact with the tissue when the tissue is placed between the jaws, and therefore impede further proximal movement of the tissue. Unfortunately, the tissue stop is sometimes ineffective to prevent rearward passage of tissue, and this, of course, can result in the transection of unstapled tissue.

Another difficulty observed in connection with the cam closure mechanism is that the opening between the jaws when the jaws are in the open position, or "gap", created when the anvil has a ramped camming surface is less than what is desired. The greater the gap, the better. This is because a wider gap enables the surgeon to more easily position the tissue between the jaws before clamping. Proper tissue positioning increases the likelihood of proper staple formation. In addition, after staples are fired, the jaws are returned to the open position, and often it is necessary to remove the spent staple cartridge and reload it with a new one for a subsequent firing. Once again, a greater gap makes it easier for the surgeon or operating room assistant to remove a spent cartridge and reload it with a new one.

Finally, the cam closure mechanism suffers from a further deficiency. If a downward force is applied to the distal end of the anvil when the end effector is positioned at the surgical site within the body cavity, the anvil will pivot from its open to closed position. This frequently occurs when the anvil brushes up against bodily tissue or organs. This inadvertent closure can cause disruption and loss of time during a surgical procedure. Furthermore, because the anvil does not have a "positive" opening position, or securely fixed open position, the end effector is less effective as a dissector. This limits the flexibility and desirability of the instrument as a whole.

Another clamping mechanism is described in Russian Patent No. 728,848. This mechanism also has a reciprocating closure tube which moves from rearward to forward positions for pivoting an anvil from an open to closed position. Lateral pins are attached to the anvil, and the closure tube rides on these pins within slots on the closure tube. While this mechanism avoids some of the deficiencies associated with a closure mechanism which has a ramped camming surface on the anvil, it still requires relative movement between the closure tube and the anvil. Consequently, not all of the anvil may be used for staple formation. The greater anvil length may create flexing or twisting when thick tissue is clamped, potentially resulting in staple malformation. The gap between the tissue-contacting surfaces when the anvil is in the open position is still less than desirable.

Another problem which arises when tissue is clamped between the anvil and staple cartridge is that the anvil can become misaligned relative to the cartridge as the anvil is moved from its open to closed positions. This may consequently cause improper clamping of tissue, which may ultimately lead to malformed or misplaced staples in the tissue.

Therefore, in view of the deficiencies inherent in those clamping mechanisms for endoscopic surgical instruments which have been previously described, an endoscopic surgical instrument with a better clamping or grasping mechanism is desired. This clamping mechanism would cause relative movement of the jaws of the end effector of the instrument from an open position where tissue can be placed between the jaws to a closed position for clamping or grasping of that tissue. The mechanism would reduce frictional losses and therefore provide greater efficiency than those mechanisms which have been described in the literature or elsewhere. It would also take full advantage of the entire length of the upper jaw, which frequently represents the anvil, and consequently reduce flexing or twisting of the jaws when tissue is clamped. Additionally, an efficient clamping mechanism which enables the creation of a wider gap between the jaws in the open position would facilitate the positioning of tissue in the jaws as well as cartridge removal and reloading. It would also be desirable if such a clamping mechanism could be developed which provides for a positive opening between the jaws in their open position so that the jaws can be used for dissection. Furthermore, as the anvil is closed to clamp tissue, it would be desirable if a mechanism were provided to ensure proper alignment between the jaws.

SUMMARY OF THE INVENTION

In one embodiment, the invention is a surgical instrument which comprises six basic elements. These elements are the following: a) a rigid frame for gripping the instrument, b) an elongated shaft extending from the frame and having a distal end, c) an end effector extending from the shaft distal end which includes first and second jaws each having proximal and distal ends, d) a first post cooperatively engaged with the proximal end of the second jaw, e) a pusher member affixed to the proximal end of the second jaw, and f) an actuator at least partially housed in the frame.

The jaws of the end effector are moveable relative to each other from an open position for receiving bodily tissue between them to a closed position for clamping or grasping this tissue. The first jaw includes an elongated channel having a base and first and second sidewalls. Each of the sidewalls has proximal and distal ends, and the sidewalls extend from the base toward the second jaw. Each sidewall has a mutually opposed elongated slot. Each of the slots is displayed diagonally upwards from a lower most end adjacent the proximal end of the sidewall to an uppermost end toward the distal end of the sidewall. In addition, the second jaw includes a tissue-contacting surface.

The first post which is cooperatively engaged with the second jaw is received within the mutually opposed elongated slots where it can slide within the slots.

The pusher member which is affixed to the second jaw is disposed adjacent the tissue-contacting surface of the second jaw. In certain embodiments, the distal end of the elongated shaft may act as the pusher member. The pusher member is moveable from a rearward position to a forward position. When the pusher member is in the rearward position, the first pin is positioned at the lowermost ends of the slots and the distal end of the second jaw is displayed rearward of the distal end of the first jaw. When the post and the second jaw are positioned in this manner, the first and second jaws are displayed in their open position. When the pusher member is in the forward position, the first post has traveled to the uppermost ends of the slots and the distal end of the second jaw is adjacent to the distal end of the first jaw. In this position, the first and second jaws are displayed in their closed position.

The actuator is operatively connected to the pusher member in cooperation with the elongated shaft. It effects movement of the pusher member from the forward position to the rearward position. Consequently, the second jaw is moved from its opened to closed position against the stationary first jaw.

The surgical instrument of this invention includes a mechanism to more efficiently clamp or grasp tissue between the jaws of an end effector. The pusher member does not move relative to the second jaw to move the second jaw from a position spaced apart from the first jaw to a position adjacent the first jaw. Rather, the pusher member abuts the proximal end of the second jaw, so that when the pusher member moves rearwardly, the second jaw moves rearwardly in tandem. Similarly, when the pusher member moves forwardly, the second jaw moves forwardly with it. Fundamentally, the open and closed positions of the first and second jaws are created by the movement of the first post as it rides in the slot of the first sidewall from the lowermost end adjacent the proximal end of the sidewall to the uppermost end toward the sidewall distal end.

Significantly, the clamping or grasping mechanism does not use the conventional ramped camming surface to move the second jaw from its open to closed positions. Accordingly, the second jaw does not require a ramped camming surface at its proximal end, and it is unnecessary for the pusher member to move forwardly relative to the second jaw to provide a camming force on this jaw to effect closure. Therefore, the inefficiencies inherent in producing the frictional forces necessary to cam the second jaw toward its closed position have been eliminated. Ultimately, since the frictional forces have been reduced, the clamping mechanism in the surgical instrument of this invention requires the user to generate less force to clamp tissue between the jaws in comparison to the force required for the conventional camming mechanism.

The elimination of the conventional camming mechanism for clamping provides another significant benefit. Since the camming surface on the second jaw has been removed, substantially the entire length of the second jaw may be used to clamp the tissue. In fact, the pusher member which moves the jaws from their open to closed positions is positioned adjacent the tissue-contacting surface of the second jaw. The operational length of the second jaw is consequently substantially the same as the actual length of the jaw. The second jaw can therefore be fabricated from a thinner beam to reduce the weight of the instrument, and the tendency of the jaws to flex or twist when tissue is clamped between them is reduced.

Another additional benefit to the clamping mechanism of the surgical instrument of this invention is the ability to more conveniently position tissue between the jaws when the jaws are in their open position. This is so because the second jaw is positioned rearwardly of the distal end of the first jaw when the jaws are in their open position. This rearward positioning of the second jaw creates a wider gap between the jaws in the open position, and therefore enhances the ability of the user of the instrument to position the tissue between the jaws. When the first jaw includes a staple cartridge received in the elongated channel of the first jaw, it also enhances the user's ability to remove a spent cartridge from the channel and reload it with a new one.

Finally, since the pusher member is affixed to the proximal end of the second jaw, the second jaw will remain in its open position until the actuator is manipulated to effect movement of the pusher member. In contrast, the camming mechanism of the prior art typically relied on a spring bias to maintain the second jaw in its spaced apart position. As such, it could easily be moved to a closed position adjacent the first jaw when the user did not want it to be moved to this position. In other words, the clamping or grasping mechanism incorporated into the surgical instrument of this invention provides a secure opening, and therefore provides greater reliability when the jaws are being positioned to manipulate tissue in varied ways during the surgical procedure.

In another embodiment, the invention is a surgical stapling instrument which comprises an elongated staple cartridge and an elongated anvil. The elongated staple cartridge has a cartridge clamping surface on it, and a cartridge alignment surface on it at a proximal end of the elongated staple cartridge. The cartridge alignment surface is adjacent the cartridge clamping surface. The cartridge alignment surface contains an alignment groove embedded within the surface. The elongated anvil has an anvil clamping surface on it facing the cartridge clamping surface. It also has an anvil alignment surface on it at a proximal end of the surface. The anvil alignment surface is adjacent the anvil clamping surface. The anvil alignment surface contains a pair of spaced-apart alignment ribs protruding from the surface.

The elongated anvil is movable relative to the elongated staple cartridge from a rearward position in which the cartridge and anvil clamping surfaces are spaced from each other for insertion of tissue between the surfaces to a forward position in which the cartridge and anvil clamping surfaces are adjacent to each other for clamping the tissue. When the elongated anvil is moved from the rearward position to the forward position, the alignment ribs on the anvil alignment surface are received into and slide within the alignment groove in the cartridge alignment surface.

The interaction between the alignment ribs on the anvil alignment surface of the anvil with the alignment groove within the cartridge alignment surface of the cartridge when the anvil is moved from its rearward to forward positions significantly minimizes or prevents misalignment of the two jaws when tissue is clamped. Consequently, the tissue is properly clamped between the jaws, and the misfiring or malformation of staples when the instrument is fired can be significantly reduced.

The surgical instrument of this invention derives its greatest benefit and is primarily adapted for endoscopic surgical procedures. However, it is entirely foreseeable and within the scope of this invention to find applications for the surgical instrument for this invention in not only endoscopic surgical procedures, but also conventional open surgical procedures as well.

BRIEF DESCRIPTION OF THE DRAWINGS

FIG. 4 is an assembled perspective view of the end effector including the pusher member in its rearward position and the jaws in their open position for receiving bodily tissue therebetween.

FIG. 5 is an assembled perspective view of the end effector including the pusher member in its forward position and the jaws in their closed position for clamping the bodily tissue.

FIG. 12 is a plan view of the staple cartridge illustrated in FIG. 8.

FIG. 13 is a side elevational view of the staple cartridge of FIG. 12.

FIG. 14 is an end elevational view of the staple cartridge taken along line 14—4 of FIG. 13.

FIG. 15 is a side elevational view of the anvil illustrated in FIG. 8 when the anvil is subjected to a load from the clamping of tissue. Indicated in phantom line is the anvil's shape when the load is not present.

FIG. 16 is a bottom plan view of the anvil of FIG. 15.

FIG. 17 is a section view taken along line 17—17 of FIG. 15.

DETAILED DESCRIPTION OF THE PREFERRED EMBODIMENT

Figure 1:
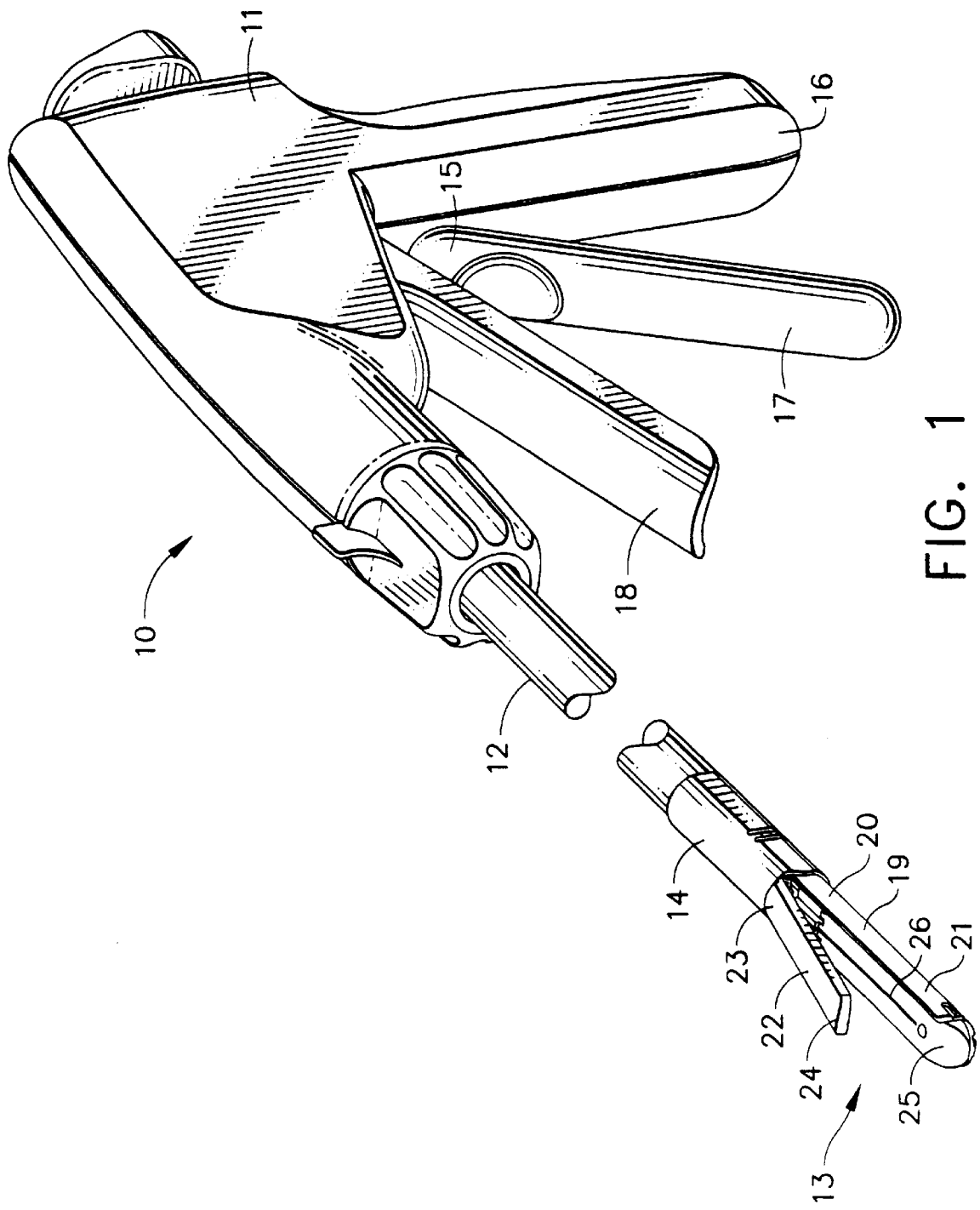
FIG. 1 is a perspective view of the most preferred surgical instrument of the invention, which is an endoscopic linear cutter.

Referring initially to FIG. 1, there is shown a general illustration of an endoscopic linear cutter 10 which is the preferred surgical instrument of this invention. The cutter has a rigid frame 11 for gripping the instrument, an elongated shaft 12 in the form of a cylindrical tube extending from the frame, and an end effector 13 attached to the distal end 14 of the shaft. The frame has an actuator 15 which is operatively connected to the end effector for activating the clamping and firing mechanisms of the end effector. The actuator includes a palm grip handle 16, a clamping trigger 17 and a firing trigger 18. The end effector includes a first jaw 19 having proximal and distal ends 20 and 21, respectively. Similarly, the end effector includes a second jaw 22 having proximal and distal ends 23 and 24, respectively. The first jaw is shaped in the form of an elongated channel for receiving a staple cartridge 25 (slots for staples not shown). The staple cartridge has a longitudinal slot 26 for the passage of a knife blade (not shown) to cut the fastened tissue between rows of formed staples. The second jaw represents an anvil against which the staples are formed. When the clamping trigger is squeezed against the palm grip handle, tissue which is positioned between the cartridge and anvil is clamped. Once the tissue is clamped, the firing trigger can then be squeezed against the clamping trigger to fire staples from the cartridge and through the tissue for formation of the staples against the anvil. To facilitate the use of the cutter in an endoscopic surgical procedure, the elongated shaft 12 is an elongated cylindrical tube which can be fitted through a trocar cannula. Endoscopic linear cutters are well known, and the details of particular clamping and firing mechanisms are described in numerous patents. For example, see U.S. Pat. Nos. 5,040,715 and 5,307,976.

Figure 2:
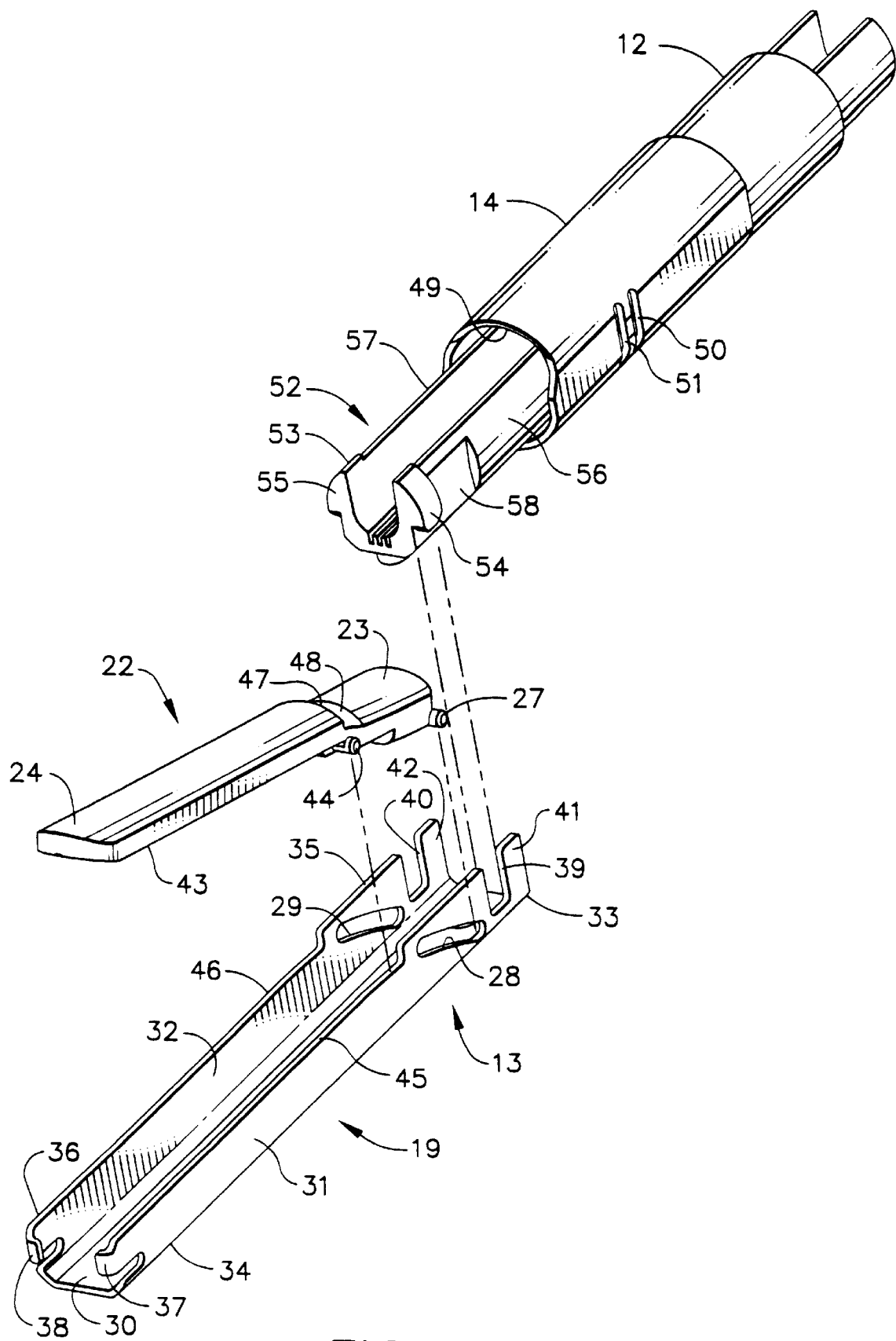
FIG. 2 is an exploded perspective view of the end effector of the linear cutter.
Figure 3:
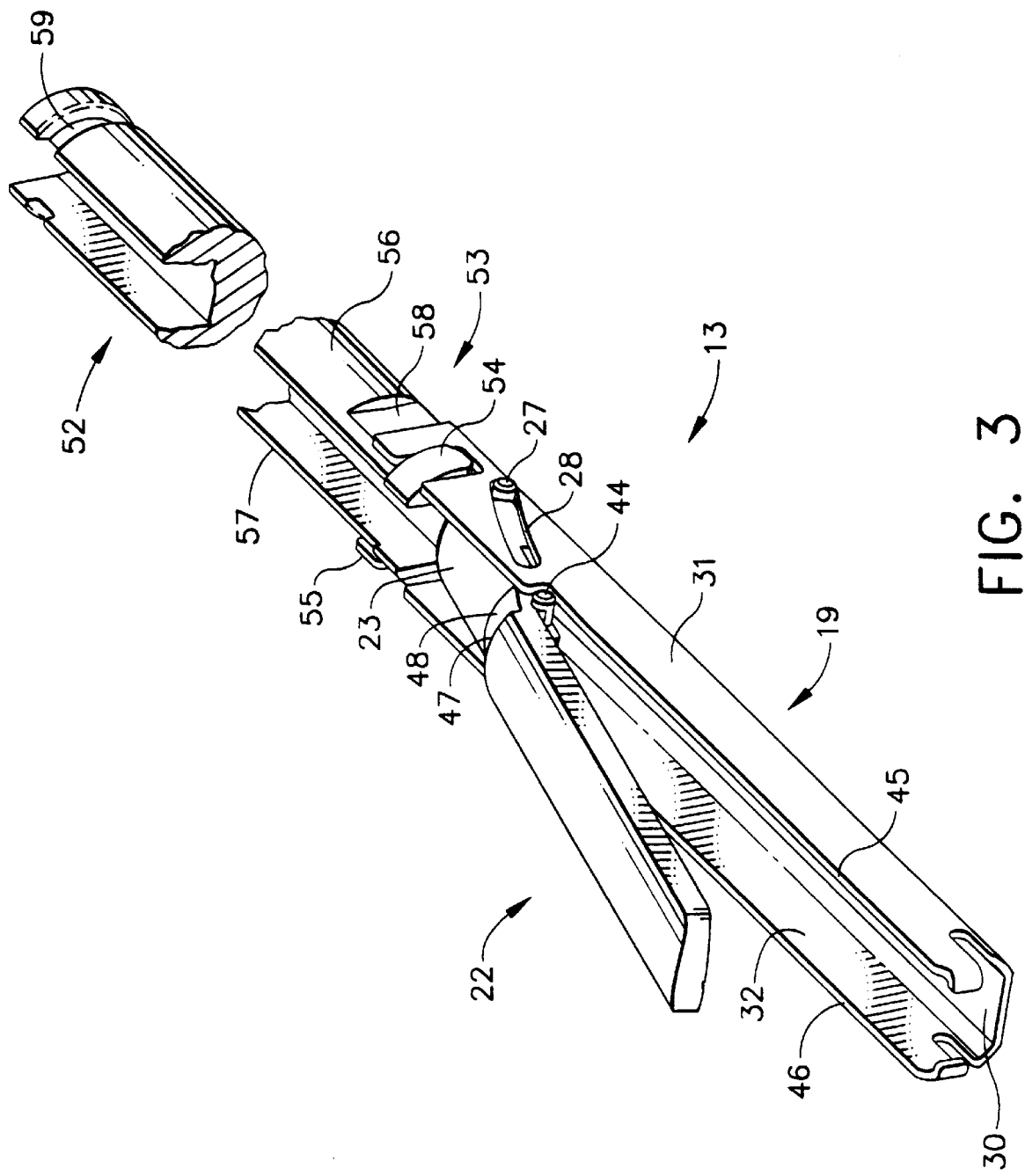
FIG. 3 is an assembled perspective view of the end effector of the linear cutter.

Referring to FIGS. 2 and 3, the details of the end effector 13 are illustrated. The primary components of the end effector are the elongated channel 19 which represents the first jaw, the anvil 22 which represents the second jaw, the first slot post 27 attached to the proximal end 23 of the anvil for cooperative sliding movement within a pair of anvil guide slots 28 and 29, respectively, and the cylindrical tube 12, which in this particularly preferred embodiment acts as the pusher member for moving the anvil relative to the channel from its open to closed positions. For simplicity and clarity, the staple cartridge 25 shown in FIG. 1 which fits into the elongated channel is not shown.

The elongated channel 19 has a base 30 and first and second sidewalls 31 and 32, respectively. The first sidewall has proximal and distal ends 33 and 34, respectively. Likewise, the second sidewall has proximal and distal ends 35 and 36, respectively. The sidewalls oppose each other and extend from the base in a generally parallel relationship toward the anvil. A staple cartridge can be inserted into the channel so that the bottom of the cartridge sits on the base and the sides of the cartridge fit snugly against the interior walls of the sidewalls of the channel. First and second cartridge clips 37 and 38, respectively, at the distal end of the sidewalls insure a tight fit of the cartridge when it is snapped into the channel. The first and second elongated, anvil guide slots 28 and 29 are displayed on the first and second sidewalls, respectively. Each sidewall extends diagonally upward from a lowermost end adjacent the proximal end 33 of the sidewall to an uppermost end which is positioned distally of the lowermost end. Adjacent the proximal end of each sidewall, there are first and second retainer slots 39 and 40, respectively, and first and second retainer clips 41 and 42, respectively.

The anvil has a tissue contacting surface 43 which faces the elongated channel. Adjacent the proximal end of the tissue-contacting surface, there are two posts which are attached to the anvil. The first post 27 is a long slot post attached at the proximal-most position on the anvil and received in the first and second anvil guide slots of the channel. The second post 44 is a shorter slide post positioned distally of the first post. The second post rests on first and second slide surfaces 45 and 46, respectively, of the sidewalls of the channel when tissue is not present between the jaws. On the surface of the anvil opposite that of the tissue-contacting surface, there is a closure tube bearing surface 47 and a chamfer ramp 48.

The distal end 13 of the closure tube 12 cooperates with the anvil to move the anvil from open to closed positions relative to the elongated channel. Accordingly, it has an anvil thrust surface 49 in contact with the closure tube bearing surface 47 of the anvil, and a chamfered surface embedded on the interior of the distal end of the closure tube (not shown) which likewise cooperates with the chamfer ramp of the anvil. There are first and second securement slots 50 and 51, respectively, displayed on the distal end of the closure tube which are used to secure the tube to the anvil. The manner in which the securement slots are used to secure the tube to the anvil is illustrated and described in more detail in connection with the discussion of FIGS. 4 and 5 below.

The elongated channel 19 is affixed to the distal end of the shaft of the instrument to a retainer rod 52. The retainer rod is housed within the elongated shaft, or in other words, it is fitted within the hollow interior of the cylindrical tube which functions as the pusher member. The retainer rod has a channel retainer 53 at its distal end. The channel retainer consists of first and second solid, arcuate surfaces 54 and 55, respectively, extending radially outwardly from first and second retainer walls 56 and 57, respectively. The channel retainer also includes a first indent portion 58 and a second indent portion (not shown) disposed within the first and second retainer walls, respectively. The channel retainer is fitted into the first and second retainer slots 39 and 40 at the proximal end of the elongated channel, and the first and second retainer clips 41 and 42 are biased against the first and second indents on the retainer walls. In this manner, the distal end of the retainer rod is attached to the proximal end of the elongated channel. Finally, at the proximal end of the retainer rod (FIG. 3), there is a rod retention groove 59. This groove facilitates the attachment of the proximal end of the rod within the frame 11 of the instrument to prevent axial movement of the rod while simultaneously permitting rotational movement.

FIGS. 4 and 5 illustrate the positional relationship between the elongated channel 19 and anvil 22 in the open and closed positions. First, it should be emphasized that there is substantially no relative movement between the closure tube and the anvil when the jaws are moved from the open to closed positions. In other words, as the closure tube moves forwardly, the anvil moves forwardly in tandem. Likewise, as the closure tube moves rearwardly, the anvil moves rearwardly as well. An anvil retainer detent 60 is created to affix the distal end 14 of the closure tube to the anvil when that portion of the closure tube positioned between the first and second securement slots 50 and 51 (FIG. 2) is crimped.

Referring now specifically to FIG. 4, the closure tube is shown in its rearward position. In this position, the first slot post is positioned within the lowermost end of the anvil guide slots on the sidewalls of the channel and the jaws are in their open position. In the open position, the anvil is spaced apart from the elongated channel, and the distal end 24 of the anvil is rearward of the distal end 21 of the channel. Turning to FIG. 5, when the closure tube is moved forwardly to its forward position, the jaws are in their closed position. The first slot post rides in the anvil guide slots from the lowermost end to the uppermost end on the sidewalls, and the second slide post slides on the first and second slide surfaces 45 and 46 of the channel in a distal direction during opening of the jaws when tissue is not present. When the jaws are in the closed position, the anvil is adjacent to the channel. When tissue is present, the second slide post may be lifted off the slide surfaces 45 and 46 of the channel, due to the resistance of the tissue to clamping. In addition, since the closure tube and anvil have moved forwardly in tandem, the distal end of the anvil is no longer rearward of the distal end of the channel, but rather the distal ends of the anvil and channel are substantially coincident with each other.

Figure 6:
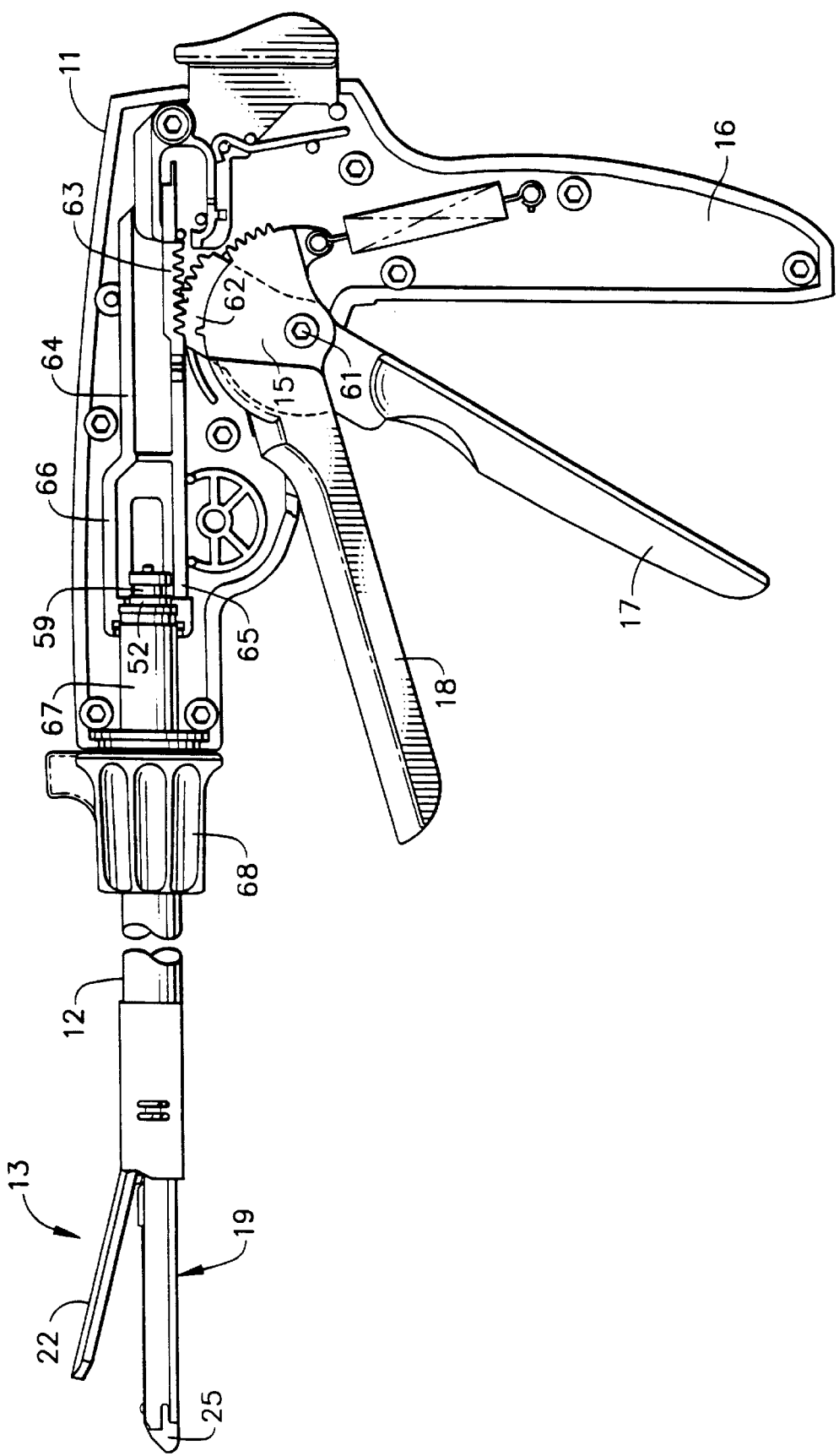
FIG. 6 is a side elevation of the endoscopic linear cutter with the top half of the molded frame and the top half of the actuator for the pusher member removed. The instrument is shown with the jaws in their open position. The distal end has been foreshortened for clarity.
Figure 7:
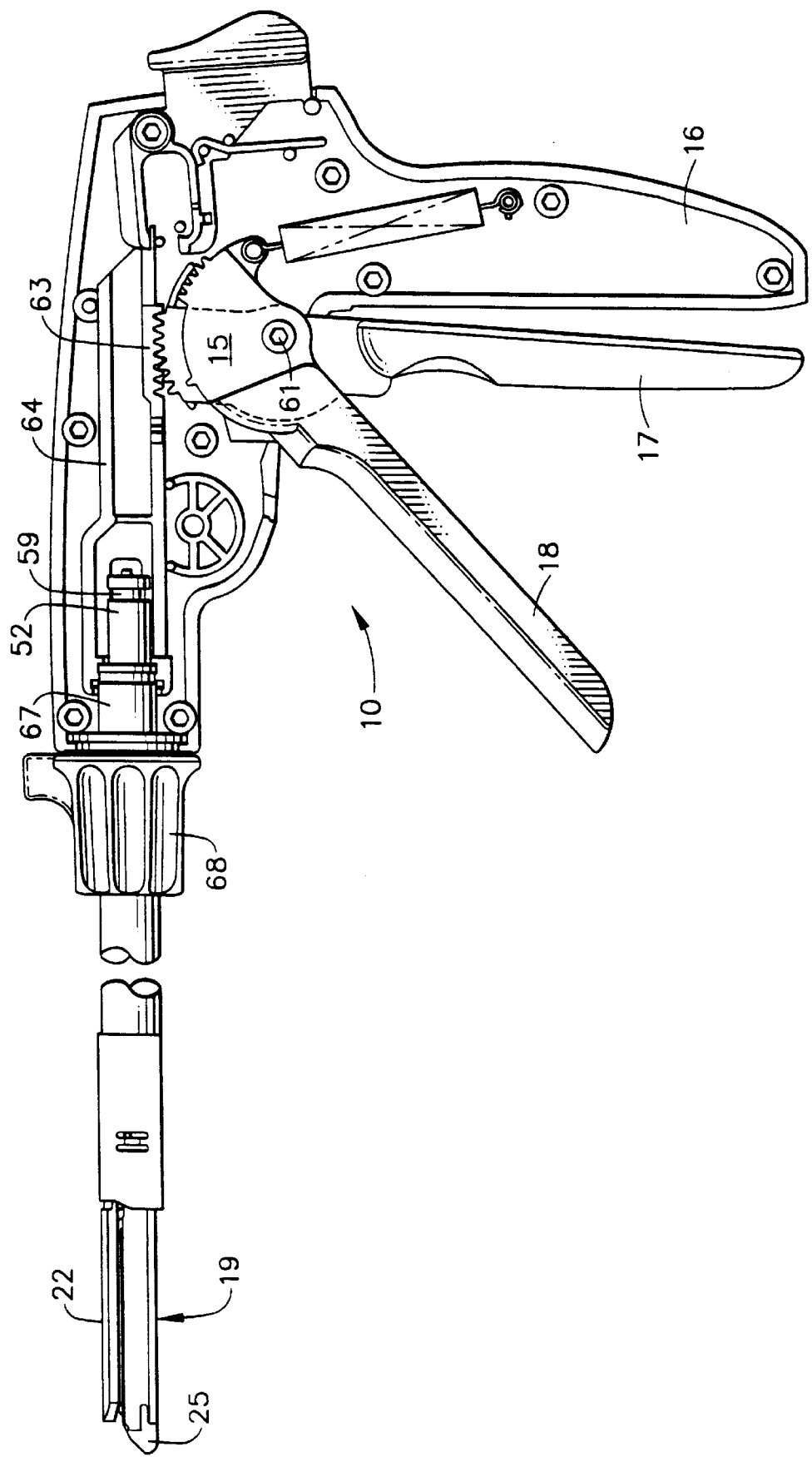
FIG. 7 is a side elevation of the endoscopic linear cutter with the top half of the molded frame and the top half of the actuator for the pusher member removed. The instrument is shown with its clamping trigger compressed and its firing trigger in its firing position. Accordingly, the instrument is shown with the jaws in their closed position. The distal end has been foreshortened for clarity.

Referring to FIGS. 6 and 7, there is shown the clamping sequence to move the jaws from an open position for inserting bodily tissue between the jaws, to a closed position for clamping the tissue. When the clamping trigger 17 of the actuator 15 is squeezed against the palm grip handle 16, the closure tube 12 is caused to move from its rearward position to its forward position to consequently move the anvil from a position spaced from the cartridge-filled channel to a position adjacent the channel. In FIG. 6 and 7, the bottom half of the frame is illustrated. The top half of the frame can be simply molded to the bottom half to completely enclose the mechanisms for clamping and firing. When the clamping trigger 17 is squeezed, it pivots about a bearing pin 61. A closure pinion 62 cooperates with an actuator rack 63, and the actuator rack moves longitudinally forward. The actuator rack is a component of a closure tube actuator 64. The closure tube actuator has at its distal end first and second arms 65 and 66, respectively, which are affixed to the proximal end 67 of the closure tube. Consequently, as the clamping trigger is squeezed and the actuator rack moves forwardly, the closure tube actuator likewise moves forwardly to move the closure tube from its rearward to forward positions. The retention rod 52 is fixed to the frame because the rod retention groove 59 comes into contact with first and second mating bosses on the bottom and top halves of the frame (not shown). This particular configuration enables the retention rod to remain in an axially fixed position, yet allows the user to rotate the retention rod, closure tube and end effector by rotating a rotation knob 68. Once the clamping trigger has been squeezed to clamp tissue between the jaws, the firing trigger can subsequently be squeezed to fire staples into the tissue while simultaneously cutting between rows of staples. Further details of the mechanism for clamping the tissue between the jaws, and the structure and mechanisms for firing and cutting the tissue are described in commonly assigned, U.S. Pat. No. 5,465,895.

Figure 8:
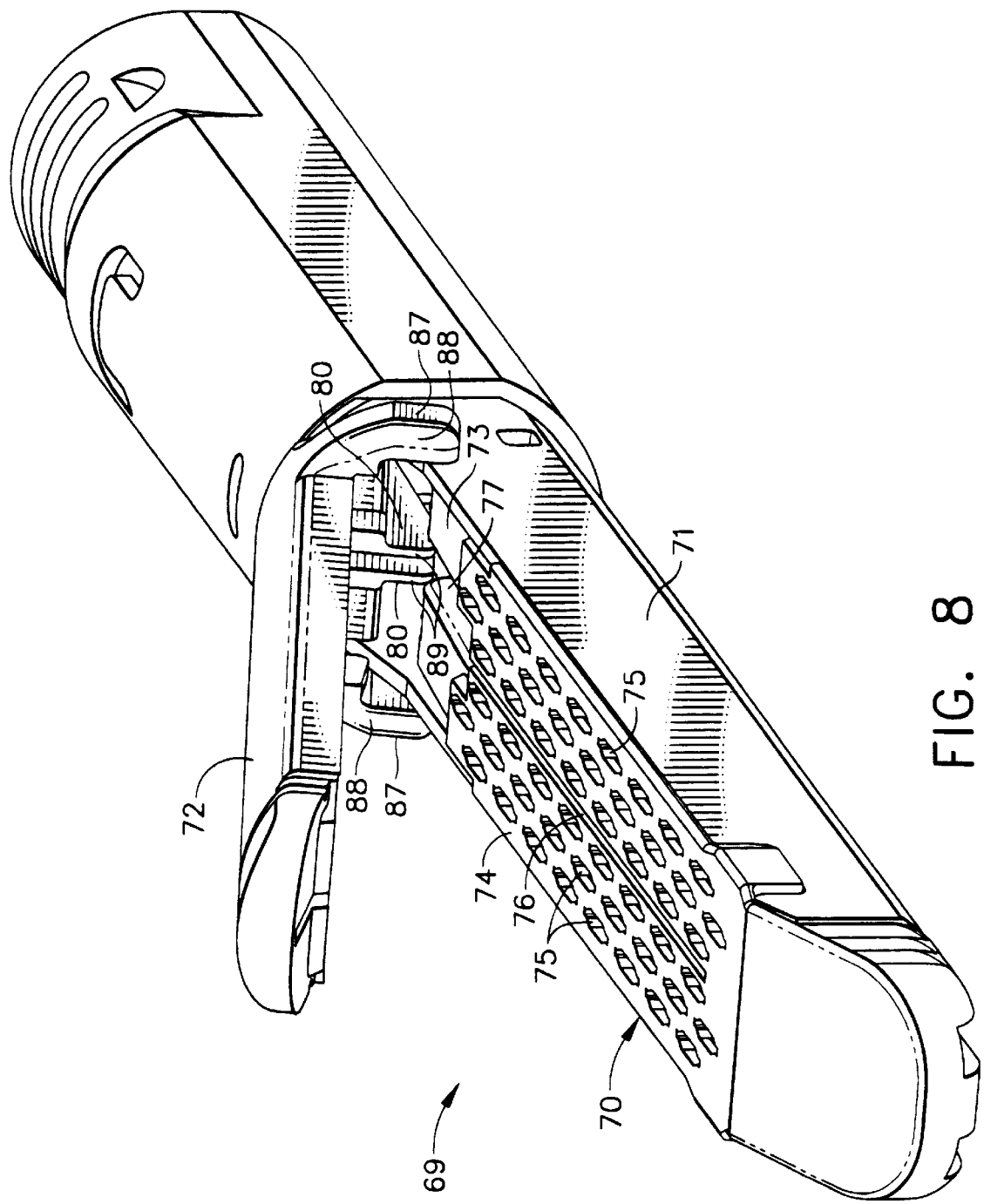
FIG. 8 is a perspective view of a preferred end effector for an endoscopic linear cutter in the form of a surgical fastening assembly which includes a staple cartridge seated in a cartridge channel, and an anvil.
Figure 9:
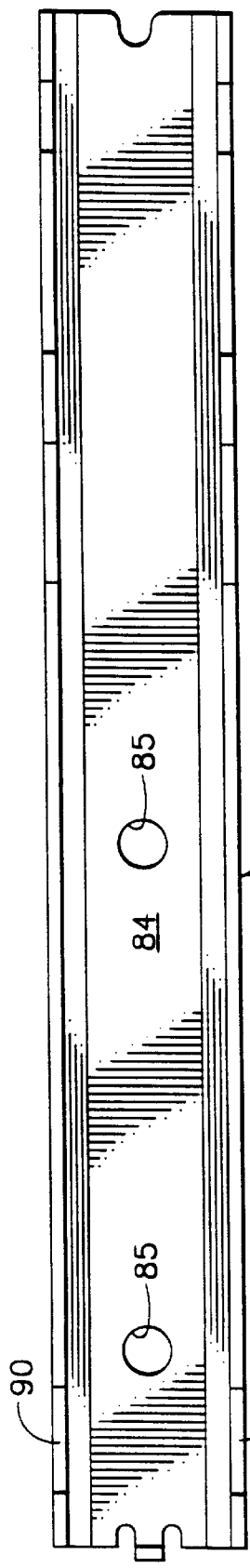
FIG. 9 is a plan view of the cartridge channel illustrated in FIG. 8.
Figure 10:
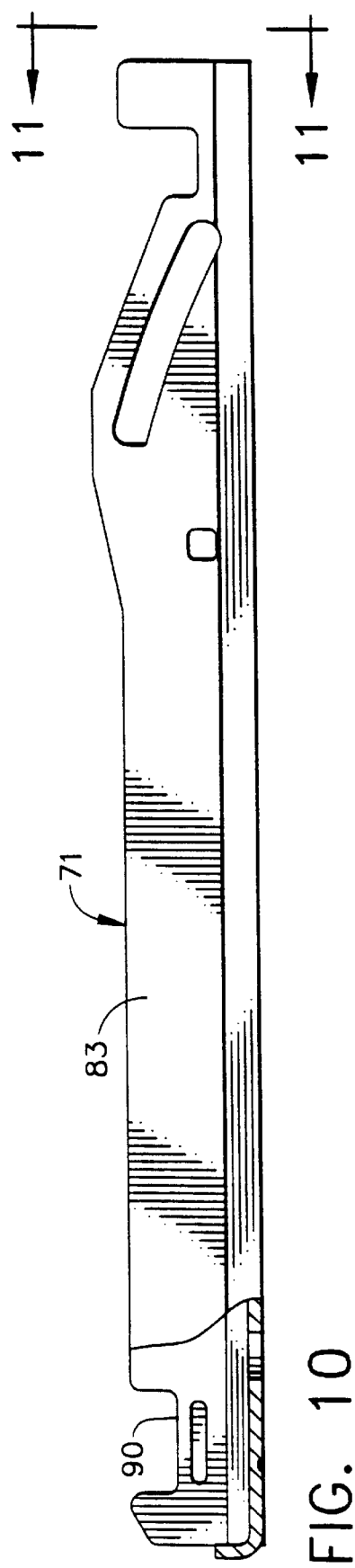
FIG. 10 is a side elevation view of the cartridge channel of FIG. 9 with a left end portion of the front wall broken away for clarity.
Figure 11:
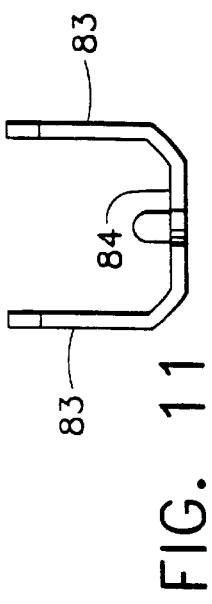
FIG. 11 is an end elevational view of the cartridge channel taken along line 11—11 of FIG. 10.

FIG. 8 illustrates a preferred end effector of the endoscopic linear cutter of this invention in the form of a surgical fastening assembly 69. The assembly has an elongated staple cartridge 70 fitted into a cartridge channel 71. The staple cartridge faces an elongated anvil 72.

The details of the elongated staple cartridge are illustrated in FIG. 8 in combination with FIGS. 12–14. The cartridge has a cartridge alignment surface 73 at its proximal end. Extending distally from the cartridge alignment surface is a generally planar cartridge clamping surface 74. Three offset, vertical rows of staple slots 75 are embedded within the cartridge clamping surface on each side of a knife slot 76 likewise embedded in the cartridge clamping surface. Each staple slot houses a staple (not shown) which is ejected for formation against the anvil, when the cutter is fired.

The staple cartridge contains an alignment groove 77 embedded within the cartridge alignment surface 73 of the cartridge. The cartridge knife slot 76 is likewise embedded within the alignment groove, and consequently extends from the proximal end of the cartridge alignment surface to adjacent the distal end of the cartridge clamping surface of the cartridge. When the cutter is fired, a cutting knife (not shown) slides distally within the knife slot through the cartridge to cut the tissue between each of the sets of three rows of staples which have been fired to fasten the tissue.

The elongated anvil 72 of the fastening assembly 69 is illustrated in detail in FIG. 8 in combination with FIGS. 15–17. The elongated anvil has an anvil alignment surface 78 at its proximal end, and an anvil clamping surface 79 extending distally from the alignment surface. The alignment and clamping surfaces of the anvil and staple cartridge are positioned to face each other, and the surfaces of each component are mutually opposed. The anvil alignment surface does not interact directly with a mating surface of the cartridge, but rather gives rise to alignment features as follows. The anvil alignment surface has a pair of spaced-apart alignment ribs 80 projecting from the anvil alignment surface towards the cartridge alignment surface. The alignment ribs are preferably shaped and sized identically to each other, and are designed to be received into and slide within the alignment groove in the cartridge alignment surface. The anvil clamping surface has two sets of three offset, vertical rows of staple-forming pockets 81 which mate with the corresponding staple slots embedded within the cartridge clamping surface of the cartridge. When staples are ejected from their slots in the cartridge, the staples are formed against the anvil within their respective staple forming pockets. An anvil knife slot 82 is embedded within the anvil and extends from the proximal end of the anvil alignment surface to adjacent the distal end of the anvil clamping surface. The anvil knife slot is situated between the spaced-apart alignment ribs, and separates the two sets of three rows of staple-forming pockets embedded within the anvil clamping surface.

Referring briefly to FIGS. 9–11 and 13, there is shown the cartridge channel 71 for removably housing the disposable cartridge. The channel has first and second spaced-apart sidewalls 83 separated by a cartridge seating surface 84. The channel is sized to securely seat the cartridge on the cartridge seating surface between the first and second sidewalls. To facilitate the proper placement of the cartridge in the cartridge channel, the cartridge channel has two notches 90 which receive corresponding locating tabs 91 displayed on the sides of the cartridge 70. To further facilitate proper placement, the cartridge seating surface has cartridge clearance holes 85 which receive pins 86 displayed on the underside of the cartridge.

When the anvil is moved forwardly to clamp tissue between the clamping surfaces of the anvil and cartridge as illustrated in FIGS. 4–7, the pair of alignment ribs protruding from the anvil alignment surface are received into and slide through the alignment groove embedded within the cartridge alignment surface of the cartridge. In this manner, the tendency of the anvil to misalign when it is moved from its open position to its closed position in response to the clamping of tissue may be reduced. When the anvil is in its closed position, and the clamping surfaces of the anvil and cartridge are adjacent to each other for the clamping of tissue, the stapling instrument is now ready to be fired. When fired, not only are the staples ejected to fasten the tissue, but a knife may slide distally through the fastening assembly because of the knife slot embedded within the alignment groove and between the spaced-apart alignment ribs of the cartridge and alignment surfaces, respectively.

Another potentially beneficial feature of the preferred fastener assembly 69 is illustrated in FIGS. 8 and 15–17. Specifically, when desired, the proximal end of the anvil 72 may include a pair of outboard tissue stops 87 which straddle the cartridge channel when the anvil is moved from its open to closed positions. Each outboard tissue stop has a stop leading edge 88, which in combination with leading edges 89 on the pair of alignment ribs of the anvil, significantly reduce or prevent tissue from "milking" proximally of the clamping surfaces of the anvil and cartridge. In this particular embodiment, the positioning of the leading edges is especially desirable because the outboard tissue stop leading edges are located distally of the leading edges of the alignment ribs.

Although this invention has been described in connection with its most preferred embodiment, the reader should not use this description to limit the scope of the claimed invention, which is set forth in connection with the claims appearing below. Obviously, numerous additional embodiments would be readily apparent to those skilled in this art, and would fall within the scope and spirit of the claimed invention. For example, it is contemplated that while the invention is particularly adapted for endoscopic applications, it is entirely possible that numerous applications for this invention in open surgery can be found. In addition, although the end effector has been described in connection with an endoscopic linear cutter, it is readily apparent that a myriad of end effector configurations can be used which fall within the scope of the claims which follow.

What is claimed is:

1. A surgical stapling instrument comprising:
   a) an elongated staple cartridge having a cartridge clamping surface thereon, and a cartridge alignment surface thereon at a proximal end thereof adjacent said cartridge clamping surface, said cartridge alignment surface containing an alignment groove embedded therein; and
   b) an elongated anvil having: i) an anvil clamping surface thereon facing said cartridge clamping surface, ii) an anvil alignment surface thereon at a proximal end thereof adjacent said anvil clamping surface, said anvil alignment surface containing a pair of spaced-apart alignment ribs protruding therefrom, each of said alignment ribs having a rib leading edge thereon, and iii) a pair of outboard tissue stops extending therefrom at a proximal end of said anvil clamping surface, each of said outboard stops having a stop leading edge thereon located distally of each of said rib leading edges;
   wherein said elongated anvil is movable relative to said elongated staple cartridge from a rearward position in which said cartridge and anvil clamping surfaces are spaced from each other for insertion of tissue therebetween to a forward position in which said outboard tissue stops straddle said elongated cartridge adjacent a proximal end of said cartridge clamping surface and said cartridge and anvil clamping surfaces are adjacent to each other for clamping the tissue, and when said elongated tissue is moved from said rearward to said forward positions, said alignment ribs on said anvil alignment surface are received into and slide within said alignment groove in said cartridge alignment surface.

2. The instrument of claim 1 wherein said cartridge clamping and alignment surfaces of said elongated staple cartridge have a cartridge knife slot embedded therein, and said cartridge knife slot is embedded within said alignment groove embedded in said cartridge alignment surface.

3. The instrument of claim 2 wherein said anvil clamping and alignment surfaces of said elongated anvil have an anvil knife slot embedded therein, and said anvil knife slot is located between said spaced-apart alignment ribs.

* * * * *